United States Patent [19]

Widman

[11] Patent Number: 4,671,787
[45] Date of Patent: Jun. 9, 1987

[54] SUPPORT WRAP SYSTEM FOR INTRAVENOUS TUBING

[75] Inventor: Richard M. Widman, Azusa, Calif.

[73] Assignee: Miron Aviv, San Francisco, Calif.

[21] Appl. No.: 854,038

[22] Filed: Apr. 21, 1986

Related U.S. Application Data

[63] Continuation-in-part of Ser. No. 632,942, Jul. 20, 1984.

[51] Int. Cl.⁴ ............................................. A61M 25/02
[52] U.S. Cl. ........................... 604/179; 128/DIG. 26; 128/DIG. 15
[58] Field of Search .................. 604/180, 174–179; 128/DIG. 26, DIG. 15, 133

[56] References Cited

U.S. PATENT DOCUMENTS

| | | | |
|---|---|---|---|
| 3,059,645 | 10/1962 | Hasbrouck et al. | 128/DIG. 26 X |
| 3,834,380 | 9/1974 | Boyd | 604/180 X |
| 3,878,849 | 4/1975 | Muller et al. | 604/179 |
| 4,088,136 | 5/1978 | Hasslinger et al. | 604/179 |
| 4,149,540 | 4/1979 | Hasslinger | 128/DIG. 15 |
| 4,445,894 | 5/1984 | Kovacs | 604/179 |
| 4,449,975 | 5/1984 | Perry | 604/180 |
| 4,484,914 | 11/1984 | Brown | 128/DIG. 26 |

Primary Examiner—Stephen C. Pellegrino
Attorney, Agent, or Firm—Boniard I. Brown

[57] ABSTRACT

The support wrap system is designed to secure the intravenous tubing in a non-kinked loop in a protective manner at the injection site. The wrap is made up of a length of material of a length sufficient to surround the limb at the injection site and to additionally overlap itself to at least 15% of its length. The two ends of the captured intravenous tubing loop are first captured by two flaps of material having respective pluralities of resilient engaging elements for releasably securing the flaps, located at one end of the wrap. The length of material is then wrapped around the limb to overlap the end which has captured the IV loop and then to resecure the wrap to itself by a third fastener of resilient elements.

12 Claims, 10 Drawing Figures

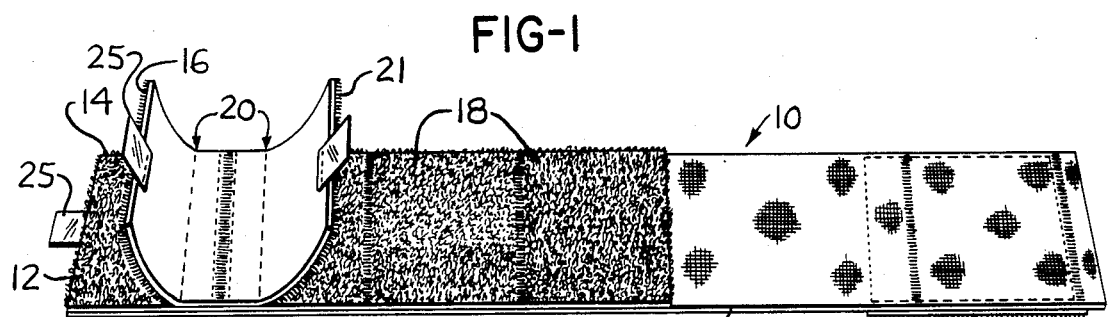
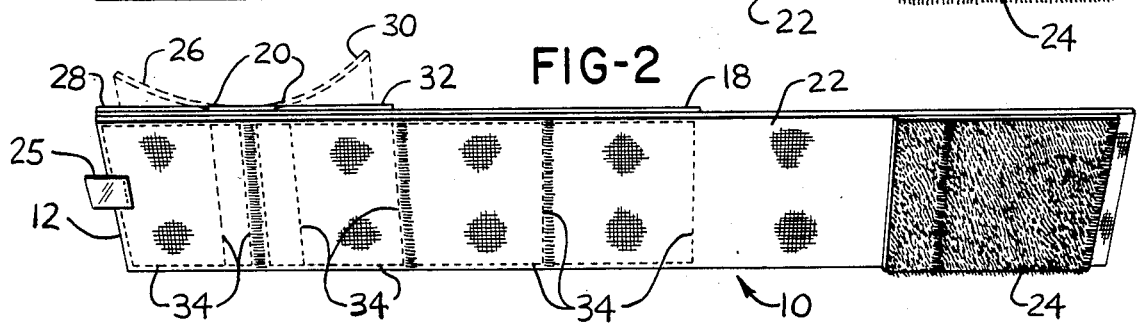
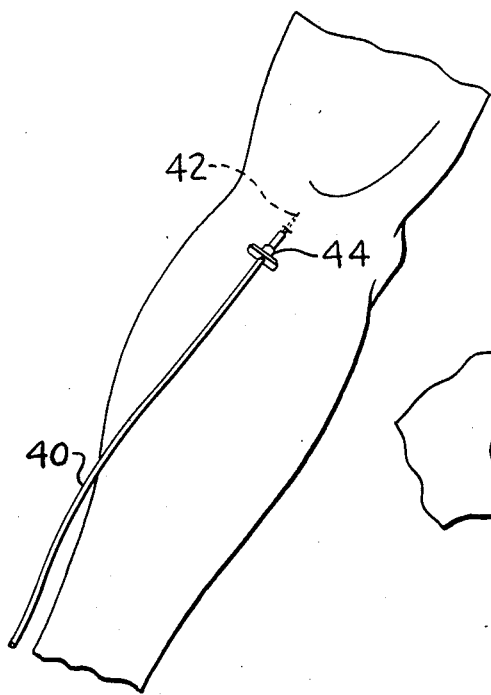
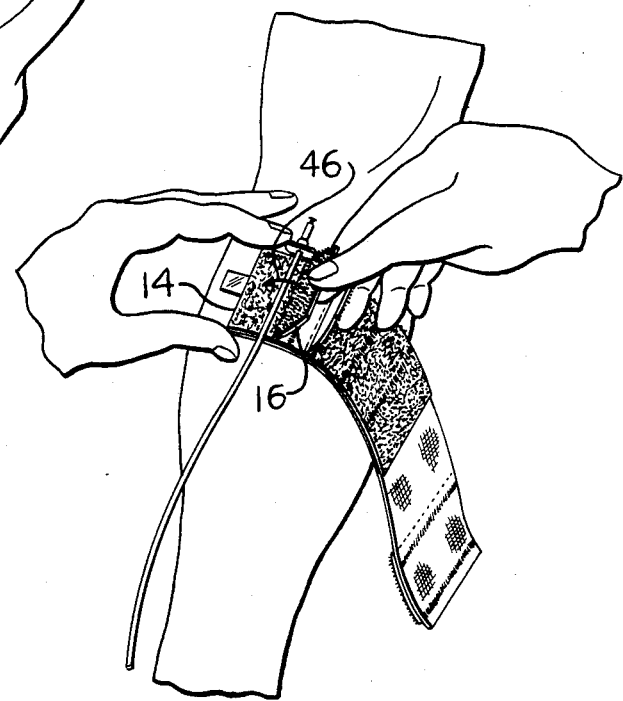

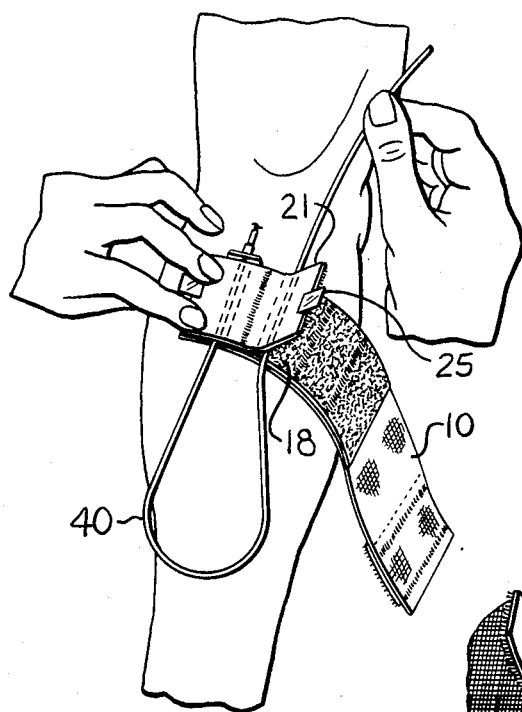
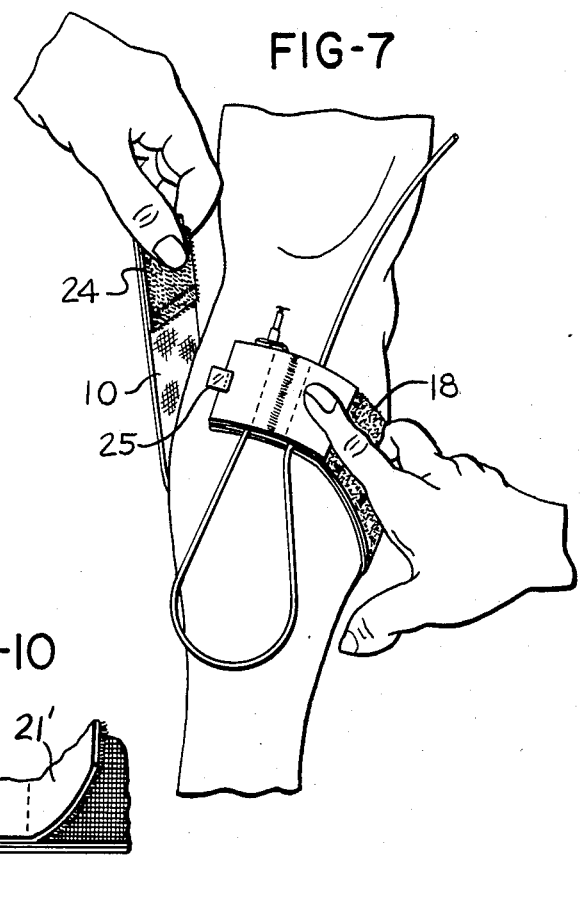
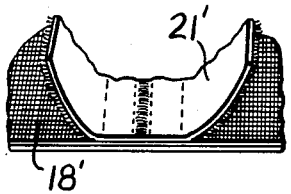
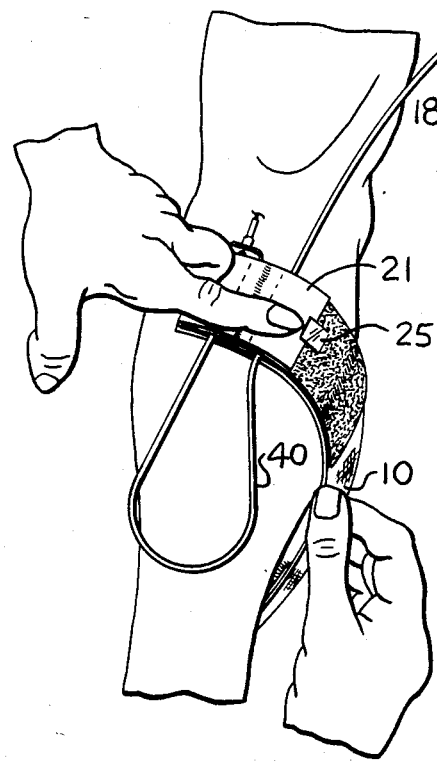
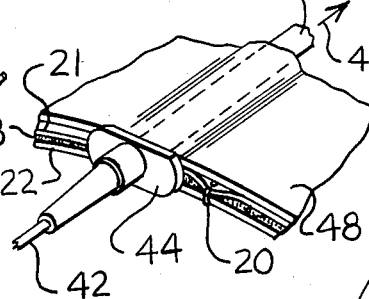
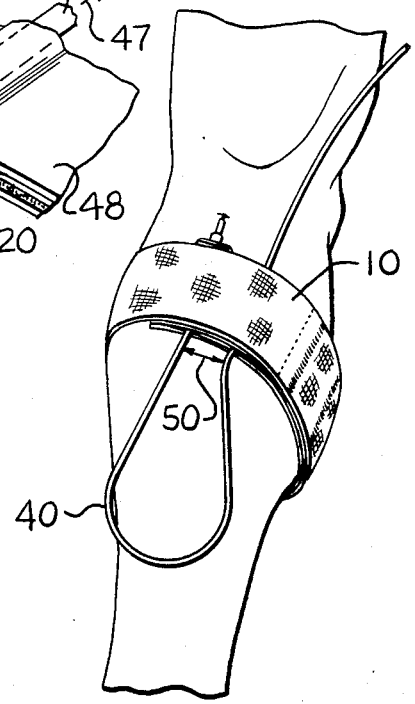

ature of this invention.

SUPPORT WRAP SYSTEM FOR INTRAVENOUS TUBING

RELATED APPLICATIONS

This application is a continuation-in-part of application Ser. No. 632,942, filed July 20, 1984.

BACKGROUND OF THE INVENTION

This invention relates to devices for holding tubular items, particularly tubular items such as intravenous tubing utilized in the field of medicine for the intravenous injection of liquids.

The most commonly used method of securing injection cannula, infusion tubes and other tubular items of equipment during intravenous injections, has been to strap such items to the patient with ordinary adhesive tape. This has proven unsatisfactory because the tape must be removed each time the held item is changed, causing discomfort to the patient and possible skin damage. Moreover, the items are usually not held sufficiently secured and are likely to move relative to the patient each time the patient moves, again causing pain and possible injury, or even complete dislodgement of the item.

One prior art tubing support system in a related field is that found in U.S. Pat. No. 3,726,280 to Lacont for a "Catheter Support" in which en elongated elastic band is used to encircle the limb and then to double back upon itself to capture the catheter tubes by a system of VELCRO (a Registered Trademark of Velcro Corporation, New York, N.Y.)-type hook and loop fasteners. Another prior art supporting system is that found in U.S. Pat. No. 3,834,380 to Boyd for a "Holder For Intravenous Injection Cannula and Tubing" which discloses a holder comprising a strip of adhesively backed tape to which is attached a longitudinally split clamping tube of flexible plastic material which receives the IV tube and over which a flap of hook and loop fastener is secured to retain the tubing within the clamping tube.

SUMMARY OF THE INVENTION

The intravenous tubing support system of this invention is made up of a flat, elongate, flexible and elastic strip of material of sufficient length to encircle the limb of the patient such that the material overlaps itself by at least 15% of its length. Attached to the end of the material which is overlapped are first and second fastener assemblies constructed of respective engagable upper and lower respective pluralities of resilient engaging elements which are separated by a distance sufficient to ensure that the captured loop of the IV tubing remains unkinked. The respective engaging element of the second fastener (the fastener located relatively inwardly from that end of the material) which is permanently mounted to the material extends further inwardly along the outward facing surface of the material such that the opposite end of the material may be wrapped around the limb and then over the end with the fastener elements, thereby additionally capturing the IV loop and being attached to the extended portion of the second fastener element by an additional respective fastener element on the overlapping end.

BRIEF DESCRIPTION OF THE DRAWINGS

FIG. 1 is an oblique view looking downwardly at the upper surface of one embodiment of the support wrap of this invention;

FIG. 2 is an oblique view of the underside of the embodiment shown in FIG. 1;

FIG. 3 is an isometric view showing the first of the several steps involved in the employment of the IV support wrap of this invention in which the IV tube has been initially inserted into a vessel in the elbow region of the right arm of a patient;

FIG. 4 is a succeeding step in which the first side of the IV loop which will be formed is captured by the hook and loop fastener at the end of the support wrap;

FIG. 5 is a succeeding step in which the second side of the IV loop is captured by the second hook and fastener element at the one end of the support wrap;

FIG. 6 is a succeeding step in which the second side of the IV loop has now been firmly captured by pressing down the hook and loop fastener while the support wrap has begun to be wrapped around the arm of the patient;

FIG. 7 is a succeeding step in which the support wrap overlapping end is prepared to be attached to the underlying portion of the support wrap;

FIG. 8 shows the completed application of the support wrap in which the overlapping end of the support wrap has been securely fixed down onto the receiving portion of the respective hook and loop fastener on the underlying portion of the support wrap;

FIG. 9 is a detail of any of the preceding FIGS. 4–8 showing a flange element which is advantageously utilized in conjunction with the IV tube to prevent the IV tube from snagging and pulling out of the blood vessel of the patient; and FIG. 10 is a fragmentary view, similar to a portion of FIG. 1, showing a woven material utilized instead of the loop fastener material of FIG. 1.

DETAILED DESCRIPTION OF THE INVENTION

This support wrap is designed to support an intravenous injection needle and tube for intravenous therapy procedures. The device serves to secure the needle and tube and to protect the venipuncture site which is prone to being bumped or contacted by objects in such a manner as to cause trauma to the lining of the venal wall, tissue damage, pain, discomfort and other adverse affects to the patient. The support wrap may be utilized in the arm, wrist, hand or leg of a patient, as necessary. The support wrap is capable of encircling a variety of different sizes of limbs; however, it is envisioned that several different standard sizes of the support wrap be employed to handle respective ranges of sizes of limbs. The support wrap is designed to capture a loop of the IV tubing rather than only a single segment thereof since this results in a much more secure retention system for the IV tubing. The loop capturing fasteners at the one end of the support wrap of this invention are designed to be at a sufficient distance apart from one another that even if the loop is somehow pulled tight against the support wrap, the tubing will not kink and thereby prevent the continued flow of the theraputic liquid into the blood vessel of the patient.

This support wrap is designed to be employed in most usages with VELCRO-type hook and loop fasteners. Such separable fasteners have gained wide acceptance for a variety of usages because of the properties of the mating hooks and loops. A surface defined by the hooks is merely placed into face-to-face relationship with a surface defined by the loops such that a large number of hooks engage a large number of loops and therefore are able to resist separation by forces parallel to the interfacial plane of engagement but are readily separable by peeling forces applied substantially normal to this interfacial plane. These fastening devices are generally formed of a sheet of synthetic woven or knitted fabric having raised threads of synthetic material, such as nylon, which are napped or unnapped to provide a pile surface defined by a plurality of loops. The other element of the fastener comprising the sheet of hooks may be formed by a variety of methods. In any event, these VELCRO-type hook and loop fasteners are especially suitable for medical applications because they are washable and flexible as well as easily applied and removed. Nevertheless, additional fastener means such as pronged metal clips may also be employed in conjunction with the support wrap of this invention to reinforce the holding power of the VELCRO fasteners. The significant consideration is that the flaps at the one end of the support wrap are securely fastened down to the underlying material of the support wrap itself such that the intravenous tubing loop is securely confined beneath the flaps of the first and second fastener elements.

Turning now to the drawings, FIG. 1 shows a view looking downwardly on the upper side of the support wrap 10 illustrated in this particular embodiment. The overlapped end 12 of the support wrap has mounted thereon the first and second fastener assemblies. The first fastener assembly comprises the two sub-elements of the separable hook and pile fastener assembly shown as the hook element 16 which forms the flap portion of the fastener and the underlying loop element 14 which is permanently attached to the underlying material of the support wrap 10. The inward portion of the upper sub-element 16 of the first fastener assembly is permanently attached along a hinge line 20 which is perpendicular to the long axis of the underlying material 22 which extends along the entire elongate length of the support wrap 10. Inwardly disposed from this hinge line 20 is the second fastener assembly defined by its upper flap sub-element 21 here formed of a corresponding element of hook material 21 and the underlying sub-element 18 formed of the loop material corresponding to the loop material element 14 of the first fastener assembly. Here also the underlying loop element 18 is permanently attached to the underlying material 22. Notice also that the loop element 18 extends further inwardly from the hinge line 20 substantially past the limit of the upper element of the second fastener assembly 21. This extension is designed to receive the corresponding third fastener element 24 which comprises a segment of the hook assembly which is permanently attached to the underside of the underlying material 22. Also shown in this figure are the tab elements 25 attached to the distal ends of the flaps 16 and 21 as well as the end 12 of the underlying wrap. These tabs facilitate the opening and closing of the VELCRO elements.

FIG. 2 shows the underside of the support wrap 10. This figure shows in more detail the attachment of the hook fastener element 24 to the underside of the supporting material 22. Additionally shown herein are the two positions of the respective first and second fastener assemblies at the other end 12 of the support wrap. The unsecured position 26 of the flap sub-element of the first fastener assembly as well as its secured position 28 are shown as well as the hinge lines 20 of the two fastener assemblies and the unsecured position 30 and secured position of the flap element of the second fastener assembly. Shown also is the extended position of the loop element 18 shown in FIG. 1. The various dotted lines labeled 34 represent preferred stitching lines utilized to permanently attach the various elements to the underlined material 22.

FIG. 3 shows the initial emplacement of an IV tube 40 into a blood vessel into the arm of a patient by the emplacement of the IV needle 42 shown in dotted lines as being inserted under the skin of the patient Shown also in this view is a flange element 44 which is attached to the IV tubing approximate to the needle 42 which serves to prevent the IV tubing from being pulled through the fastener elements of the support wrap as shown in the succeeding drawing figures.

FIG. 4 shows the first step in the emplacement of the support wrap. The first leg of the IV loop is captured between the upper flap sub-element 16 of the first fastener assembly by folding down the hook elements of the flap 16 in the direction of the arrow 46 onto the receiving loop elements 14.

FIG. 5 shows the next step in the emplacement of the support wrap 10 in which the loop is now formed in the IV tube 40 by placing the second leg of the IV tubing into the second fastener assembly defined between the upper flap 21 and the receiving loop element 18 of the second fastener assembly.

FIG. 6 shows the capturing of the second leg of the IV loop 40 beneath the flap 21 of the second fastener element as the remainder of the support wrap 10 is wrapped around the arm of the patient.

FIG. 7 shows the support wrap 10 almost completely encircling the limb of the patient with the third fastener element 24 formed here of the hook portion of the VELCRO fasteners. This end with the VELCRO hook element 24 will then be wrapped over the top of the two fastener assemblies to engage into the still uncovered portion of the loop elements 18.

FIG. 8 shows the completed application of the support wrap with the loop of the IV tubing 40 being securely confined by the support wrap 10. The distance 50 is sufficient to prevent kinking of the loop 40 should running end (the end leading away from the patient) be pulled up tight, thereby collapsing the loop.

FIG. 9 is a detail of the various preceding FIGS. 4–8 showing the operation of the flange 44 which acts to prevent the pulling of the IV tube 40 and the needle 42 out of the blood vessel should forces be applied to the tubing in the direction of the arrow 47. This figure is also of interest for its display of the various layers of the support wrap in its applied configuration. Illustrated herein are one hinge line 20, the underlying material 22, the layer of loop material 18 as well as the overlying flap of hook material 21 and also the overlapping end of the support wrap 10 here labeled as 48, although actually consisting of the same material as the underlying material labeled 22. This underlying material is desirably flexible, somewhat elastic and washable. The elastic property allows for the wrap to be firmly emplaced without restricting the circulation in the limb of the patient.

FIG. 10 shows, in a fragmentary view, similar to a portion of FIG. 1, an embodiment of the invention wherein the resilient engaging elements of the first and second fastener assemblies comprise hook-type elements on upper element 21', as with the embodiment of FIG. 1, which mate with engaging elements in the form of resilient projections of or from a woven material.

It will be appreciated that any resilient engaging elements which are readily securable in opposing or confronting relation and which resist forces in the transverse direction parallel in the plane of engagement, may be utilized within the scope of the present invention. A relatively inexpensive type of engaging elements can be provided by multi-filamentary yarns brushed or napped to provide a fuzzy, piled surface which readily engages the hook fastener elements, much like the engagement of VELCRO ® brand woven loop material. Examples of knitted fastener elements are shown and described in U.S. Pat. Nos. 3,530,687 and 3,539,436. Examples of hook engaging elements are described in U.S. Pat. Nos. 3,138,841, 3,320,649, 3,718,725, and 3,770,359.

There has been shown and described a novel support wrap system which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

The inventor claims:

1. A support system for intravenous tubing employed to inject liquids into a vessel in a limb of a patient comprising a flat, elongate, flexible elastic strip of material of sufficient length to encircle the limb in the vicinity of the injected vessel such that the material overlaps itself by at least 15% of its length to which is attached towards the one end which is overlapped on the surface away from the limb, first and second fastener assemblies constructed of respective engagable upper and lower hook and loop elements, the first fastener assembly being located proximate to the overlapped end and having a permanently closed hinge line perpendicular to the long axis of the material joining the upper and lower hook and loop elements which is located at the inward edge of the first fastener assembly relative to the end and the second fastener assembly opening towards the other end of the material with its permanently closed hinge line located at a sufficient distance from the first hinge line such that an unkinked loop may be formed in the IV tubing when it is captured by the two fastener assemblies and wherein the underlying respective hook or loop element of the second fastener assembly extends beyond the end of the respective engaging upper element of the second fastener assembly to a point near the midpoint of the material such that it may engage with a third respective hook or loop element which is attached to the other side of the other end of the material when the material is overlappingly wrapped around the limb to cover over the two fastener assemblies which act to hold the IV tubing loop.

2. The support system of claim 1 wherein the underlying elements of the first and second fastener assemblies comprise loop elements which are permanently attached to the underlying material and wherein the upper fastener elements of the first and second fastener assemblies comprise hook elements and wherein the third fastener element attached to the other end of the material comprises a hook element.

3. The support system of claim 1 wherein the underlying elements of the first and second fastener assemblies comprise hook elements which are permanently attached to the underlying material and wherein the upper fastener elements of the first and second fastener assemblies comprise loop elements and wherein the third fastener element attached to the other end of the material comprises a loop element.

4. The system of claim 1 wherein the distal ends of the upper fastener elements of the first and second fastener assemblies comprise a tab element extending outwardly therefrom.

5. The system of claim 4 wherein the distan end of the underlying element of the first fastener assenbly also comprises a tab element.

6. A support system for intravenous tubing employed to inject liquids into a vessel in a limb of a patient comprising a flat, elongate, flexible strip of material of sufficient length to encircle the limb in the vicinity of the injected vessel such that the material overlaps itself by at least 15% of its length to which is attached towards the one end which is overlapped on the surface away from the limb, first and second fastener assemblies, each of said fastener assemblies comprising upper and lower elements having opposed surfaces each having a respective plurality of resilient engaging elements thereon which are engagable for releasably securing the upper and lower elements together, the first fastener assembly being located proximate to the overlapped end and having a permanently closed hinge line perpendicular to the long axis of the material joining the upper and lower elements which is located at the inward edge of the first fastener assembly relative to the end and the second fastener assembly opening towards the other end of the material with its permanently closed hinge line located at a sufficient distance from the first hinge line such that an unkinked loop may be formed in the IV tubing when it is captured by the two fastener assemblies and wherein the underlying respective engaging element of the second fastener assembly extends beyond the end of the respective engaging upper element of the second fastener assembly to a point near the midpoint of the material such that it may engage with a third respective element which is attached to the other side of the other end of the material when the material is overlappingly wrapped around the limb to cover over the two fastener assemblies which act to hold the IV tubing loop.

7. The support system of claim 6 wherein the underlying elements of the first and second fastener assemblies comprise projections of a woven material, and wherein the upper fastener elements of the first and second fastener assemblies comprise hook elements and wherein the third fastener element attached to the other end of the material comprises a hook element.

8. The support system of claim 6 wherein the underlying elements of the first and second fastener assemblies comprise projections of a fuzzy, piled fabric surface, and wherein the upper fastener elements of the first and second fastener assemblies comprise hook elements and wherein the third fastener element attached to the other end of the material comprises a hook element.

9. The support system of claim 6 wherein the underlying elements of the first and second fastener assemblies comprise hook elements which are permanently attached to the underlying material and wherein the upper fastener elements of the first and second fastener assemblies comprise projections of a woven material and wherein the third fastener element attached to the other end of the material comprises projections of a woven material.

10. The support system of claim 6 wherein the underlying elements of the first and second fastener assemblies comprise hook elements which are permanently attached to the underlying material and wherein the upper fastener elements of the first and second fastener assemblies comprise projections of a fuzzy, piled material surface and wherein the third fastener element attached to the other end of the material comprises projections of a fuzzy, piled material.

11. The system of claim 6 wherein the distal ends of the upper fastener elements of the first and second fastener assemblies comprise a tab element extending outwardly therefrom.

12. The system of claim 6 wherein the distal end of the underlying element of the first fastener assembly also comprises a tab element.

* * * * *